United States Patent [19]

Monte

[11] Patent Number: 5,424,299
[45] Date of Patent: Jun. 13, 1995

[54] COMPOSITION AND METHOD FOR REJUVENATING ENTERAL FEEDING TUBES

[76] Inventor: Woodrow C. Monte, 6411 S. River Dr., #65, Tempe, Ariz. 85283

[21] Appl. No.: 51,229

[22] Filed: Apr. 23, 1993

[51] Int. Cl.⁶ .................. A61M 5/00; A23L 3/34; A61K 37/18; A61K 37/02
[52] U.S. Cl. .................. 514/54; 426/335; 426/532; 426/656; 426/658; 604/158; 604/159; 604/163; 604/164; 604/170; 604/171; 604/267
[58] Field of Search .................. 514/54; 426/335, 532, 426/656, 658; 604/267, 159, 164, 170, 171, 158, 163

[56] References Cited

U.S. PATENT DOCUMENTS

| | | | |
|---|---|---|---|
| 4,142,999 | 3/1979 | Bloching et al. | 252/544 |
| 4,753,963 | 6/1988 | Jandacek et al. | 514/558 |
| 4,894,056 | 1/1990 | Bommarito | 604/267 |
| 4,931,300 | 6/1990 | Monte | 426/335 |
| 4,959,350 | 9/1990 | Frokjaer et al. | 514/21 |
| 5,032,297 | 7/1991 | Williamson et al. | 252/8.551 |
| 5,104,677 | 4/1992 | Behr et al. | 426/590 |
| 5,156,875 | 10/1992 | Monte | 426/532 |
| 5,221,668 | 6/1993 | Henningfield et al. | 514/23 |

*Primary Examiner*—Ronald W. Griffin
*Attorney, Agent, or Firm*—Tod R. Nissle

[57] ABSTRACT

An ingestible rejuvenation composition is injected into an enteral feeding tube to clean remnant food from the tube and decontaminate the tube. The rejuvenation composition includes a carrier, edible acids, enzymes for degrading the remnant food, and an edible antimicrobial agent.

20 Claims, No Drawings

COMPOSITION AND METHOD FOR REJUVENATING ENTERAL FEEDING TUBES

This invention relates to methods and compositions for rejuvenating enteral feeding tubes.

More particularly, the invention relates to a method and composition for cleaning and disinfecting an enteral feeding tube while the tube remains inserted in a patient.

In a further respect, the invention relates to an enteral cleaning composition which can be safely ingested by a patient.

The administration through enteral feeding tubes of aqueous solutions of nutritionally balanced food compositions are known in the art. For example, my U.S. Pat. No. 4,931,300 for "ANTIMICROBIAL FOOD COMPOSITION" discloses a food composition which can be administered through an enteral feeding tube.

During the use of enteral feeding tubes, residual food proteins, starches, and cellulose often accumulate in and block the feeding tube. In addition to preventing food composition from passing through the tube to the stomach, such blockages also provide a ready site for the growth and multiplication of bacteria. Cleaning an enteral feeding tube is a time consuming procedure because the tube must first be removed from the patient, which gives the patient discomfort. After being removed, pressurized fluids and other equipment must be utilized to ream residual food compositions from the tube and disinfect the tube. After the feeding tube is cleaned, it is reinserted via the nose and esophagus of the patient, causing the patient additional discomfort.

Accordingly, it would be highly desirable to provide a method for cleaning residual food compositions from an enteral feeding tube which would not require that the tube be removed from the patient, which would not require access to pressurized fluids and other equipment for cleaning the enteral feeding tube, and which would decontaminate the feeding tube.

Therefore, it is a principal object of the invention to provide an improved method and composition for removing residual food from an enteral feeding tube.

Another object of the invention is to provide a composition which decontaminates an enteral cleaning tube and synergistically reacts with residual food in the enteral cleaning tube to produce food by-products which are more readily digested than the original residual food.

A further object of the invention is to provide an enteral feeding tube cleaning composition which does not utilize toxic cleaning agents and which can safely be ingested by a patient.

These and other, further and more specific object and advantages of the invention will be apparent to those skilled in the art from the following detailed description thereof.

Briefly, I have discovered an ingestible composition for decontaminating and cleaning an enteral feeding tube. The composition includes from 1% to 95% by weight of carbohydrates selected from the group consisting of corn syrup solids, trisaccharides, tetrasaccharides, pentasaccharides, hexasaccharides, dextrose, fructose, sucrose, maltose, oligosaccharides and higher saccharides; from 0.005% to 10% by weight of at least one enzyme in the group consisting of protein hydrolyzing enzymes, starch dextrinizing enzymes, starch saccharifying enzymes, and cellulose hydrolyzing enzymes; from 0.1% to 8% by weight of an edible acid for adjusting the pH of the composition within the range of 2 to 6.5; and, from 0.001% to 6% by weight of an antimicrobial agent selected from the group consisting of sorbic acid, benzoic acid, sodium benzoate, potassium sorbate, sodium sorbate, and potassium benzoate. The composition can be in liquid form and include water and have a viscosity in the range of 10 to 20,000 centipoise at 76 degrees Fahrenheit.

In another embodiment of the invention, I have discovered an ingestible composition for decontaminating and cleaning an enteral feeding tube. The composition includes from 45% to 90% by weight of an ingestible carrier; from 0.005% to 10% by weight of at least one enzyme in the group consisting of protein hydrolyzing enzymes, starch dextrinizing enzymes, starch saccharifying enzymes, and cellulose hydrolyzing enzymes; from 0.1% to 8% by weight of an edible acid for adjusting the pH of the food composition within the range of 2 to 6.5; from 0.01% to 6% by weight of an antimicrobial agent selected from the group consisting of sorbic acid, benzoic acid, sodium benzoate, potassium sorbate, sodium sorbate, and potassium benzoate; and, from 0.005% to 5% by weight of an ingestible gum. The ingestible composition can include from 0.005% to 5% by weight of an ingestible gum and can be in liquid form and include water; and, have a viscosity greater than about 2.0 at 76 degrees Fahrenheit.

In still another embodiment of the invention, I discovered a method for cleaning residual food from inside an enteral feeding tube and for decontaminating the feeding tube. The method includes the step of manufacturing an ingestible composition. The ingestible composition consists of from 45% to 90% by weight of an ingestible carrier; from 0.005% to 10% by weight of at least one enzyme in the group consisting of protein hydrolyzing enzymes, starch dextrinizing enzymes, starch saccharifying enzymes, and cellulose hydrolyzing enzymes; from 0.1% to 8% by weight of an edible acid for adjusting the pH of the food composition within the range of 2 to 6.5; from 0.01% to 6% by weight of an antimicrobial agent selected from the group consisting of sorbic acid, benzoic acid, sodium benzoate, potassium sorbate, sodium sorbate, and potassium benzoate. The ingestible composition is injected into the enteral feeding tube. The ingestible composition can include from 0.005% to 5.0% by weight of an ingestible gum. The ingestible composition can be in liquid form and include water.

When carbohydrates are utilized as a carrier, they may be any of the digestible carbohydrates such as dextrose, fructose, sucrose, maltose, oligosaccharides, high saccharides, or mixtures thereof, depending on usage. The carbohydrates help disperse the enzymes when water is added to the powdered composition. Any other non-toxic, ingestible carrier can be utilized.

The powder form of the composition has a relatively low moisture content. The moisture content is, as is the case for many powdered formulations, preferably at least below 4% by weight and more preferably below 3% by weight. Such low moisture content provides a product having a shelf life of at least one year shelf stability at ambient conditions if hermetically sealed.

As noted, the powdered form of the food composition may be reconstituted with a liquid. The powder is ordinarily partially dissolved and partially suspended in the resulting liquid form of the invention. While it is possible to reconstitute the composition with liquid such as alcohol, the reconstituting liquid will ordinarily be water. The water may contain additional ingredients such as alcohol, glycerol, propylene glycol, sugars and flavor.

The edible acidulants which can be utilized in the powder composition of the invention include malic acid, acetic acid, citric acid, lactic acid, sodium acetate, fumaric acid, ascorbic acid, or an acidic salt such as sodium acetate in order to adjust the pH within the range of 2 to 6.5. This pH is critical because it reduces microbial activity and facilitates decontamination of the enteral feeding tube. A pH greater than 6.5 is not acceptable because a low pH is necessary to reduce antimicrobial activity.

The antimicrobial activity of sorbic and benzoic acid is due primarily to the undissociated acid molecule. Antimicrobial activity is therefore pH dependent and the estimated activity at any pH can be estimated as shown below in Table I.

TABLE I

EFFECT OF pH ON DISSOCIATION

| pH | Percent Undissociated Acid | |
|---|---|---|
| | Sorbic | Benzoic |
| 3 | 98 | 94 |
| 4 | 86 | 60 |
| 5 | 37 | 13 |
| 6 | 6 | 1.5 |
| 7 | 0.6 | 0.15 |

The benzoates and sorbates are important in the composition of the invention because at low pH values in the range of 2 to 6.5 they provide significant antimicrobial activity.

The powder composition of the invention includes at least one enzyme in the group consisting of protein hydrolyzing enzymes, starch dextrinizing enzymes, starch saccharifying enzymes, and cellulose hydrolyzing enzymes. These enzymes are critical in the practice of the invention because they facilitate the hydrolysis or degradation of food proteins, starches, and cellulose. An acid resistant protease enzyme is presently preferred to hydrolyze or degrade proteins. For example, the PAPAIN enzyme preparation produced by Solvay Enzymes is a good grade proteolytic enzyme preparation which is isolated from the latex of the Carica papaya fruit. The enzyme has a broad substrate specificity and is capable of hydrolyzing small peptides as well as proteins. Hydrolysis can proceed to the amino acid stage but not necessarily to completion. The broad substrate specificity of the PAPAIN enzyme preparation enables the enzyme to easily and efficiently hydrolyze most soluble proteins. The optimum pH range of PAPAIN is generally 5.0 to 7.0. The effective pH range is 3.5 to 9.0. The enzyme portion of PAPAIN is readily water soluble.

An acid resistant alpha amylase enzyme is presently preferred to hydrolyze or degrade starches. For example, the CLARASE fungal alpha-amylase enzyme produced by Solvay Enzymes is obtained by the controlled fermentation of *Aspergillus oryzae* var. CLARASE complies with FCC and FAO/WHO recommended specifications for food grade enzymes. The alpha-amylase is characterize by both dextrinizing (liquefying) and saccharifying (glucose and maltose liberating) actions on starch. The enzyme is an endoamylase capable of rapidly hydrolyzing the interior alpha-1,4-glucosidic linkages of starch, glycogen and their degradation products. CLARASE alpha-amylase initially hydrolyzes starch solutions yielding soluble dextrins and oligosaccharides (dextrinizing action). Prolonged hydrolysis with CLARASE alpha-amylase results in the formation of substantial quantities of glucose and maltose (saccharifying action). The maximum activity for CLARASE alpha-amylase occurs in the range of pH 4.8 to 5.4. The enzyme can effectively hydrolyze starch over a range of 4.0 to 6.6. In addition to alpha-amylase activity, CLARASE is characterize by significant proteolytic activity. Acylase, maltase, phosphatase, cellulase, sulfatase, transglucosidase, and alpha-glucosidase have been detect as trace activities. The enzyme portion of CLARASE is readily water soluble.

The presently preferred acid resistant food grade enzyme for degrading cellulose by converting it to glucose is CELLULASE 4000, also produced by Solvay Enzymes. CELLULASE 4000 contains at least three distinct enzyme components which degrade cellulose. The Cl component of CELLULASE 4000 apparently disrupts the structure of native cellulose by weakening the hydrogen bonds. This action is required before hydrolysis of highly structured forms of cellulose (cotton, crystalline cellulose, wood, etc.) can occur. The Cx component of CELLULASE 4000 consists of Beta-1,4-glucanases. Exo-Beta-1,4-glucanase successively removes single glucose units from the nonreducing end of the cellulose chain, while endo-Beta-1,4-glucanases randomly hydrolyze the interior glucosidic bonds of cellulose liberating oligomers of lower molecular weight. The Beta-glucosidase components, including celloblase, of the CELLULASE 4000 are primarily active on the smaller molecular weight cellulose hydrolysates. During cellulose breakdown they are active on the dimers and oligomers of cellulose. The CELLULASE 4000 enzyme is stable in solution over the range of about pH 3.0 to 8.0, and has an optimum pH range of 3.5 to 5.0. CELLULASE 4000 also has significant hemicellulase activity which has an optimum pH range of 3.5 to 4.5. Alpha amylase, Beta galactosidase, Beta glucanase, glucoamylase, glucose oxidase, pectinase, protease, and xylanase have been detected as trace activities in CELLULASE 4000. The enzyme portion of CELLULASE is readily water soluble.

EDTA, cysteine, and other similar sequestering agents can be included in the powder composition of the invention to sequester metal ions which inhibit the effectiveness of CELLULASE, PAPAIN, CLARASE, or other enzymes which may utilized in the practice of the invention. Such sequestering of metal ions prevents the metals ions from reacting with the enzymes and inhibiting the effectiveness of the enzymes. Sequestering agents are usually present in a concentration of 0.001% to 4.00% by weight.

A surfactant like sodium lauryl sulfate can be included in the powder composition to facilitate the degradation of food product blocking or adhering to the interior of the enteral feeding tube. Such surfactants are present in the powder rejuvenation composition in a concentration in the range of 0.001% to 5.00% by weight.

Buffers like disodium phosphate-dihydrate can be included in the powder composition of the invention to stabilize the pH of the solution when the solution is introduced into an enteral feeding tube. Such buffers are present in the powder rejuvenation composition in a concentration in the range of 0.05% to 10% by weight.

When it is desired to increase the viscosity of the solution which results after the powder composition is reconstituted with water, xanthan gum, carrageenin or another thickener can be included in the powder composition. Such thickeners are normally present in the powder rejuvenation composition in a concentration in the range of 0.50% to 12.0% by weight.

When the powder rejuvenation composition of the invention is reconstituted with water, the amount of water used with a selected weight of powder can vary as desired. When, for example, it is desired to make the resulting aqueous solution more viscous so it better adheres to the internal surfaces of the feeding tube and to residual food in the feeding tube, the quantity of water can be reduced.

The following examples depict the presently preferred embodiments of the invention for the purposes of illustrating the practice thereof and not by way of limitation of the scope of the invention. In the examples, all proportions are by weight, unless otherwise noted.

EXAMPLE 1

A food composition in powder form is prepared by blending the following ingredients.

| Ingredient | Weight Percent |
|---|---|
| MALTODEXTRIN (POLYSACCHARIDES) | 31.00000 |
| MALTODEXTRIN AGGLOMERATED | 24.00000 |
| MCT OIL | 6.70000 |
| CORN OIL | 6.70000 |
| WHEY PROTEIN POWDER | 9.30000 |
| HYDROLYZED PROTEIN POWDER (dipeptides, tripeptides, oligopeptides) | 9.58103 |
| SODIUM ACETATE | 0.88000 |
| POTASSIUM CITRATE | 0.57000 |
| CALCIUM PHOSPHATE | 0.70000 |
| DIPOTASSIUM PHOSPHATE | 0.80000 |
| MAGNESIUM CHLORIDE 6H | 0.90000 |
| FERROUS SULFATE | 0.01400 |
| ZINC SULFATE 1H | 0.01800 |
| MANGANESE SULFATE 1H | 0.00460 |
| CUPRIC SULFATE 5H | 0.00230 |
| CHROMIC CHLORIDE | 0.00012 |
| POTASSIUM IODIDE | 0.00005 |
| SELENIUM OXIDE | 0.00003 |
| MOLYBDENUM TRIOXIDE | 0.00003 |
| LECITHIN | 0.44000 |
| SODIUM ASCOREATE | 0.44000 |
| CHLORINE CHLORIDE | 0.21000 |
| VITAMIN E (500 IU/GM) | 0.05000 |
| NIACINAMIDE | 0.01800 |
| CALCIUM PANTOTHENATE | 0.01600 |
| THIAMINE HYDROCHLORIDE | 0.00250 |
| PYRIDOXINE HYDROCHLORIDE | 0.00300 |
| RIBOFLAVIN | 0.00180 |
| VITAMIN A (250,000 IU/GM) | 0.01000 |
| FOLIC ACID | 0.00044 |
| BIOTIN (1% 10 MG/GM) | 0.02500 |
| VITAMIN K 1% | 0.00430 |
| VITAMIN D3 (1,000,000 IU/GM) | 0.00300 |
| CYANOCOBALAMIN (0.1%) | 0.00580 |
| SOY POLYSACCHARIDE (FIBER) | 7.60000 |
| Total Weight | 100.000000 |

The approximate percent calories from the various ingredients are carbohydrates 52.4%, fat 30.5%, and protein 17.1%. The carbohydrates included in the powder food composition include sucrose, dextrose, maltose, lactose, trisaccharides, tetrasaccharides, pentasaccharides, hexasaccharides, and higher saccharides. When 25 gm of the food powder composition is reconstituted with 75 gm of water the resulting mixture has a caloric density (Cal/ml) of 1.07; a total Cal/Nitrogen ratio of 145.9; a non-protein ratio of 120.9; a protein concentration of 45.8 g/liter; a fat concentration of 36.1 g/liter; a carbohydrate (digestible) concentration of 140 g/liter; a carbohydrate (total) concentration of 153.8 g/liter; and a dietary fiber concentration of 14 g/liter.

During the blending of the above-listed ingredients of the food composition, agglomeration techniques are preferably employed to make the resulting powder mixture more easily dispersed and soluble in water.

EXAMPLE 2

One thousand grams of the food composition powder of Example 1 is mixed with three thousand grams of water. The resulting drink provides 1.1 calories per cubic centimeter, has a pH of 4.7, has an osmolarity of 300, has a viscosity of about 90 to 100 centipoise, and has particles each having a size of less than about 100 mesh.

EXAMPLE 3

One thousand grams of a food composition in powder form is prepared by blending the following ingredients in the proportions noted.

| INGREDIENT | WEIGHT PERCENT Dry |
|---|---|
| SUGAR | 5.70 |
| WHEY PROTEIN CONCENTRATE | 15.09 |
| FORETEIN 35 (protein alpha-amino acids) | |
| CALCIUM LACTATE, PENTAHYDRATE | 3.67 |
| CREATIVE CREAMER 829 (fat emulsifier) | 5.70 |
| MALTODEXTRIN, M100 (agglomerated) | 67.23 |
| HERCULES CELLULOSE GUM, CMC-7HF | 1.99 |
| EMULSIFIER, BEATREME 3581Z (fat emulsifier) | .22 |
| VITAMIN PREMIX 110584 (Vitamins A, D, C, K. etc.) | .22 |
| MAGNESIUM OXIDE | .18 |
| TOTAL | 100.00 |

The approximate percent calories from the various ingredients are carbohydrates 50%, fat 30%, and protein 18%. The carbohydrates included in the powder food composition include sucrose, dextrose, maltose, lactose, trisaccharides, tetrasaccharides, pentasaccharides, hexasaccharides, and higher saccharides. When 25 gm of the food powder composition is reconstituted with 75 gm of water the resulting mixture has a caloric density (Cal/ml) of 1; a total Cal/Nitrogen ratio of 140; a non-protein ratio of 120; a protein concentration of 45 g/liter; a fat concentration of 36 g/liter; a carbohydrate (digestible) concentration of 140 g/liter; a carbohydrate (total) concentration of 150 g/liter; and a dietary fiber concentration of 14 g/liter.

EXAMPLE 4

948 grams of food composition powder of EXAMPLE 3 are mixed with 3328 milliliters of water. The resulting drink provides about 1 calorie per cubic centimeter, has a pH of about 4.6, has an osmolarity of about 300, has a viscosity of about 90 to 100 centipoise, and has a particulate each having a size of less than about 100 mesh.

EXAMPLE 5

About five hundred milliliters of the rejuvenation solution of the invention are prepared by blending the following ingredients in the proportions noted.

| INGREDIENT | GRAMS |
|---|---|
| Maltodextrin, M100 (polysaccharides) | 32.32 |

-continued

| INGREDIENT | GRAMS |
|---|---|
| PAPAIN 30,000 pu/mg (Solvay Enzymes) | 5.11 |
| CLARASE 40,000 SKGU/gm (Solvay Enzymes) | 8.18 |
| CELLULASE 400 (Solvay Enzymes) | 0.26 |
| Xanthan Gum (KELTROL F) | 2.04 |
| Citric Acid 1 Hydrate (Acidulant) | 1.07 |
| Disodium Phosphate-Dihydrate (Buffer) | 1.74 |
| Ascorbic Acid (Acidulant) | 0.10 |
| Potassium Sorbate (Antibacterial Agent) | 0.26 |
| Sodium Lauryl Sulfate (Surfactant) | 0.04 |
| Disodium EDTA (Sequestering Agent) | 0.01 |
| Water (8.466 lb/gal; 3840 gm/gal) | 459.87 |
| TOTAL WEIGHT | 511.00 |

The rejuvenation solution has a pH of 5.2

EXAMPLE 6

About five hundred milliliters of the rejuvenation solution of the invention are prepared by blending the following ingredients in the proportions noted.

| INGREDIENT | GRAMS |
|---|---|
| Maltodextrin, M100 (polysaccharides) | 32.32 |
| PAPAIN 30,000 pu/mg (Solvay Enzymes) | 5.11 |
| CELLULASE 400 (Solvay Enzymes) | 0.26 |
| Xanthan Gum (KELTROL F) | 2.04 |
| Citric Acid 1 Hydrate (Acidulant) | 1.07 |
| Disodium Phosphate-Dihydrate (Buffer) | 1.74 |
| Ascorbic Acid (Acidulant) | 0.10 |
| Potassium Sorbate (Antibacterial Agent) | 0.26 |
| Sodium Lauryl Sulfate (Surfactant) | 0.04 |
| Disodium EDTA (Sequestering Agent) | 0.01 |
| Water (8.466 lb/gal; 3840 gm/gal) | 459.87 |
| TOTAL WEIGHT [CLARASE OMITTED] | 502.82 |

The rejuvenation solution has a pH of about 5.2.

EXAMPLE 7

About five hundred milliliters of the rejuvenation solution of the invention are prepared by blending the following ingredients in the proportions noted.

| INGREDIENT | GRAMS |
|---|---|
| Maltodextrin, M100 (polysaccharides) | 32.32 |
| PAPAIN 30,000 pu/mg (Solvay Enzymes) | 5.11 |
| CLARASE 40,000 SKGU/gm (Solvay Enzymes) | 8.18 |
| Xanthan Gum (KELTROL F) | 2.04 |
| Citric Acid 1 Hydrate (Acidulant) | 1.07 |
| Disodium Phosphate-Dihydrate (Buffer) | 1.74 |
| Ascorbic Acid (Acidulant) | 0.10 |
| Potassium Sorbate (Antibacterial Agent) | 0.26 |
| Sodium Lauryl Sulfate (Surfactant) | 0.04 |
| Disodium EDTA (Sequestering Agent) | 0.01 |
| Water (8.466 lb/gal; 3840 gm/gal) | 459.87 |
| TOTAL WEIGHT [CELLULASE OMITTED] | 510.74 |

The rejuvenation solution has a pH of about 5.2.

EXAMPLE 8

About five hundred milliliters of the rejuvenation solution of the invention are prepared by blending the following ingredients in the proportions noted.

| INGREDIENT | GRAMS |
|---|---|
| Maltodextrin, M100 (polysaccharides) | 32.32 |
| CLARASE 40,000 SKGU/gm (Solvay Enzymes) | 8.18 |
| CELLULASE 400 (Solvay Enzymes) | 0.26 |

-continued

| INGREDIENT | GRAMS |
|---|---|
| Xanthan Gum (KELTROL F) | 2.04 |
| Citric Acid 1 Hydrate (Acidulant) | 1.07 |
| Disodium Phosphate-Dihydrate (Buffer) | 1.74 |
| Ascorbic Acid (Acidulant) | 0.10 |
| Potassium Sorbate (Antibacterial Agent) | 0.26 |
| Sodium Lauryl Sulfate (Surfactant) | 0.04 |
| Disodium EDTA (Sequestering Agent) | 0.01 |
| Water (8.466 lb/gal; 3840 gm/gal) | 459.87 |
| TOTAL WEIGHT [PAPAIN OMITTED] | 505.89 |

The rejuvenation solution has a pH of about 5.2.

EXAMPLE 9

About five hundred milliliters of the rejuvenation solution of the invention are prepared by blending the following ingredients in the proportions noted.

| INGREDIENT | GRAMS |
|---|---|
| Maltodextrin, M100 (polysaccharides) | 32.32 |
| PAPAIN 30,000 pu/mg (Solvay Enzymes) | 5.11 |
| CLARASE 40,000 SKGU/gm (Solvay Enzymes) | 8.18 |
| CELLULASE 400 (Solvay Enzymes) | 0.26 |
| Citric Acid 1 Hydrate (Acidulant) | 1.07 |
| Potassium Sorbate (Antibacterial Agent) | 0.26 |
| Water (8.466 lb/gal; 3840 gm/gal) | 459.87 |
| TOTAL WEIGHT [OMITTED XANTHAN GUM, BUFFER, ASCORBIC ACID, SURFACTANT, AND SEQUESTERING AGENT] | 507.07 |

The rejuvenation solution has a pH of about 5.2.

EXAMPLE 10

About five hundred milliliters of the rejuvenation solution of the invention are prepared by blending the following ingredients in the proportions noted.

| INGREDIENT | GRAMS |
|---|---|
| Maltodextrin, M100 (polysaccharides) | 1.00 |
| PAPAIN 30,000 pu/mg (Solvay Enzymes) | 5.11 |
| CLARASE 40,000 SKGU/gm (Solvay Enzymes) | 8.18 |
| CELLULASE 400 (Solvay Enzymes) | 0.26 |
| Citric Acid 1 Hydrate (Acidulant) | 1.07 |
| Potassium Sorbate (Antibacterial Agent) | 0.26 |
| Water (8.466 lb/gal; 3840 gm/gal) | 459.87 |
| TOTAL WEIGHT [OMITTED XANTRAN GUM, BUFFER, ASCORBIC ACID, SURFACTANT, AND SEQUESTERING AGENT, AND MOST OF MALTODEXTRIN] | 507.07 |

The rejuvenation solution has a pH of about 5.3.

EXAMPLE 11

The food composition of EXAMPLE 2 is administered to a patient through a clear plastic enteral feeding tube until a clog develops in the tube. The tube extends into the stomach of the patient and has an inner diameter of about one-quarter of an inch. The clog develops when food composition no longer flows through the tube. After the clog develops, the tube is removed from the patient to determine the size of the clog. The clog extends along a length of the enteral tube equal to about one-eighth of an inch. The tube is maintained in an upright orientation similar to the orientation of the tube when inserted in the patient. Five milliliters of the rejuvenation solution of EXAMPLE 5 is injected in the upper end of the tube, flows down the tube, and comes to rest against the upper portion of the clog. After about seven minutes, the rejuvenation solution dissipates the clog and flows to the lower end of the tube.

EXAMPLE 12

EXAMPLE 11 is repeated, except the rejuvenation solution of EXAMPLE 6 is utilized instead of the solution of EXAMPLE 5. Similar results are obtained.

EXAMPLE 13

EXAMPLE 11 is repeated, except the rejuvenation solution of EXAMPLE 7 is utilized instead of the solution of EXAMPLE 5. Similar results are obtained.

EXAMPLE 14

EXAMPLE 11 is repeated, except the rejuvenation solution of EXAMPLE 8 is utilized instead of the solution of EXAMPLE 5. Similar results are obtained.

EXAMPLE 15

EXAMPLE 11 is repeated, except the rejuvenation solution of EXAMPLE 9 is utilized instead of the solution of EXAMPLE 5. Similar results are obtained, except dissolution of the clog takes longer.

EXAMPLE 16

EXAMPLE 11 is repeated, except the rejuvenation solution of EXAMPLE 10 is utilized instead of the solution of EXAMPLE 5. Similar results are obtained, except dissolution of the clog takes longer.

EXAMPLE 17

EXAMPLE 11 is repeated, except the food composition of EXAMPLE 4 is utilized instead of the food composition of EXAMPLE 2. Similar results are obtained.

EXAMPLE 18

EXAMPLE 11 is repeated, except that after the enteral feeding tube is removed to determine the magnitude of the clog, the tube is reinserted in the patient prior to inserting the rejuvenation solution in the tube. After eight minutes, food composition passes through the tube into the stomach of the patient, indicating that the clog has been dissipated by the rejuvenation solution.

EXAMPLE 19

The food composition of EXAMPLE 2 is administered to a patient through a clear plastic enteral feeding tube for several hours. The tube is then removed for inspection. The tube has an inner diameter of about one-quarter of an inch. Although the tube is not fully blocked, residual food adheres to the inside of the tube at various locations along the length of the tube. The residual food restricts the inner diameter of the tube a minor amount, i.e., about ten percent, however the food composition of EXAMPLE 2 can still travel through the enteral tube. The tube is maintained in a vertical orientation similar to the orientation of the tube when the tube is inserted in the nose, esophagus, and stomach of the patient. Ten milliliters of the rejuvenation composition of EXAMPLE 5 is directed into the upper end of the tube. Portions of the composition adhere to the residual food as the composition flows down the tube. After about one hour, the residual food has been degraded and moved to and out of the lower end of the tube with the rejuvenation composition, producing a rejuvenation composition—degraded food combination mixture in the dish underneath the lower end of the tube. A plate count is performed to determine the presence of aerobic and anaerobic bacteria. The plate count is performed by transferring one milliliter of the rejuvenation composition—degraded food mixture to a 10 milliliter enriched Thio. The Thio is incubated at 35° C. for four days to culture for anaerobes. The Thio is then examined to determine the existence of aerobic and anaerobic bacteria. The forgoing plate count procedure is carried out on accordance with the FDA Bacteriological Analytical Manual, 4th Edition, 1984, Chapter 4, and with the ASM Manual of Clinical Microbiology, 4th Edition, 1985. In the plate count less than ten aerobic organisms per gram were detected. No anaerobic bacteria were detected during the plate TABLE .I

TABLE I

PLATE COUNT RESULTS SHOWING ABSENCE OF AEROBIC BACTERIA IN MIXTURE OF REJUVENATION COMPOSITION AND DEGRADED RESIDUAL FOOD

| PLATE COUNT | DESCRIPTION | AEROBIC ORGANISMS PER MILLILITER |
|---|---|---|
| 1 | REJUV. COMP.-RESIDUAL FOOD MIX. | <10 |

EXAMPLE 20

EXAMPLE 19 is repeated except that the composition of EXAMPLE 4 is utilized in place of the composition of EXAMPLE 2. Similar results are obtained.

EXAMPLE 21

The rejuvenation composition of the invention is prepared in powder form by blending the following ingredients in the proportions noted.

| INGREDIENT | GRAMS |
|---|---|
| Maltodextrin, M100 (polysaccharides) | 32.32 |
| PAPAIN 30,000 pu/mg (Solvay Enzymes) | 5.11 |
| CLARASE 40,000 SKGU/gm (Solvay Enzymes) | 8.18 |
| CELLULASE 400 (Solvay Enzymes) | 0.26 |
| Xanthan Gum (KELTROL F) | 2.04 |
| Citric Acid 1 Hydrate (Acidulant) | 1.07 |
| Disodium Phosphate-Dihydrate (Buffer) | 1.74 |
| Ascorbic Acid (Acidulant) | 0.10 |
| Potassium Sorbate (Antibacterial Agent) | 0.26 |
| Sodium Lauryl Sulfate (Surfactant) | 0.04 |
| Disodium EDTA (Sequestering Agent) | 0.01 |
| TOTAL WEIGHT | 51.13 |

The viscosity of the reconstituted aqueous solution of the rejuvenation composition of the invention can be important. The viscosity preferably is such that the reconstituted rejuvenation composition will adhere to residual food in an enteral tube to act on and degrade the food. The viscosity at 68° F. of the reconstituted rejuvenation composition ordinarily is less than 20,000 centipoises, preferably less than about 2,000 centipoises. The viscosity of olive oil at 68° F. is 1008 millipoises; of sperm oil at 68° F. is 420 millipoises; of water at 68° F. is 10.02 millipoises; of caster oil at 68° F. is 10,272 millipoises; of turpentine at 68° F. is 14.87 millipoises; of methyl alcohol at 68° F. is 5.93 millipoises; and, of glycerol at 20° C. is 10,690 millipoises. The viscosity of glycerol at 20.9° C. is 7,776 millipoises. The preferred viscosity of the reconstituted composition of the invention will, as appreciated by those of skill in the art, vary depending on a number of factors. Such factors can include the size of the enteral tube, the food composition being administered through the tube, whether the tube is completely blocked, whether there is a large amount or a small amount of residual food, whether the reconstituted rejuvenation composition is administered with a food composition, etc. Even at low viscosities of 50 centipoises or less, the food composition of the invention retains its homogeneity. In one embodiment of the invention, the preferred viscosity is less than 50 centipoises.

Enteral tubes are used to dispense food into the esophagus, stomach, or intestinal tract of a patient.

Having described my invention in such terms as to enable those skilled in the art to understand and practice it, and having identified the presently preferred embodiments thereof, I claim:

1. An ingestible composition for decontaminating and cleaning residual food from an enteral feeding tube, said composition consisting of:
   (a) from 1% to 95% by weight of carbohydrates selected from the group consisting of corn syrup solids, trisaccharides, tetrasaccharides, pentasaccharides, hexasaccharides, dextrose, fructose, sucrose, maltose, oligosaccharides and higher saccharides;
   (b) from 0.005% to 10% by weight of enzymes for degrading at least one of the food components in the group consisting of protein, starch, and cellulose;
   (c) from 0.1% to 8% by weight of an edible acid for adjusting the pH of the composition within the range of 2 to 6;
   (d) from 0.001% to 6% by weight of an antimicrobial agent selected from the group consisting of sorbic acid, benzoic acid, sodium benzoate, potassium sorbate, sodium sorbate, and potassium benzoate.

2. The ingestible composition of claim 1 in liquid form and
   (a) including water; and,
   (b) having a viscosity in the range of 10 to 20,000 centipoise at 76 degrees Fahrenheit.

3. An ingestible food grade composition for decontaminating and cleaning an enteral feeding tube, said food grade composition consisting of:
   (a) from 45% to 90% by weight of an ingestible carrier;
   (b) from 0.005% to 10% by weight of enzymes for degrading at least one food component in the group consisting of protein, starch, and cellulose;
   (c) from 0.01% to 8% by weight of an edible acid for adjusting the pH of the food composition within the range of 2 to 6.5;
   (d) from 0.001% to 6% by weight of an antimicrobial agent selected from the group consisting of sorbic acid, benzoic acid, sodium benzoate, potassium sorbate, sodium sorbate, and potassium benzoate; and,
   (e) from 0.005% to 5% by weight of an ingestible gum.

4. The ingestible composition of claim 2 including from 0.005% to 5% by weight of an ingestible gum.

5. The ingestible composition of claim 3 in liquid form and
   (a) including water; and,
   (d) having a viscosity greater than about 2.0 at 76 degrees Fahrenheit.

6. The ingestible composition of claim 2 including from zero to 0.01% by weight of a surfactant.

7. The ingestible composition of claim 1 including from zero to 0.05% by weight of a surfactant.

8. The ingestible composition of claim 4 including from zero to 0.01% by weight of a surfactant.

9. The ingestible composition of claim 3 including from zero to 0.05% by weight of a surfactant.

10. A method for dissipating a clog in and cleaning residual food from inside an enteral feeding tube which is inserted in a patient and for killing substantially all aerobic and anerobic bacteria in the enteral feeding tube, including the steps of
    (a) providing an ingestible aqueous composition consisting of
        (i) from 45% to 90% by weight of an ingestible carrier including water;
        (ii) from 0.005% to 10% by weight of enzymes for degrading at least one food component in the group consisting of protein, starch, and cellulose;
        (iii) from 0.1% to 8% by weight of an edible acid for adjusting the pH of the food composition within the range of 2 to 6.5;
        (iv) from 0.001% to 6% by weight of at least one antimicrobial agent selected from the group consisting of sorbic acid, benzoic acid, sodium benzoate, potassium sorbate, sodium sorbate, and potassium benzoate, said antimicrobial agent killing substantially all bacteria in the enteral feeding tube when the pH of the food composition is within the range of 2 to 6.5; and,
    (b) injecting said ingestible composition into the enteral feeding tube such that said ingestible composition flows down the feeding tube, comes to rest against the occlusion, degrades the occlusion, and after several minutes dissipates the occlusion causing degraded residual food from the occlusion to flow along the feeding tube and into the digestive tract of the patient.

11. The method of claim 10 wherein in step (a), said ingestible composition includes from 0.005% to 5.0% by weight of an ingestible gum.

12. The method of claim 10 wherein in step (a), said ingestible composition is in liquid form and includes water.

13. The composition of claim 1 wherein said enzymes degrade protein, starch, and cellulose.

14. The composition of claim 3 wherein said enzymes degrade protein, starch, and cellulose.

15. The method of claim 10 wherein said enzymes degrade protein, starch, and cellulose.

16. The composition of claim 1 including 0.001% to 4.00% by weight of at least one sequestering agent.

17. The composition of claim 3 including 0.001% to 4.00% by weight of at least one sequestering agent.

18. The method of claim 10 wherein said composition includes 0.001 to 4.00% by weight of at least one sequestering agent.

19. The composition of claim 2 wherein said enzymes degrade protein, starch, and cellulose.

20. The composition of claim 19 wherein said composition includes 0.001 to 4.00% by weight of at least one sequestering agent.

* * * * *